United States Patent [19]

Price, Jr.

[11] Patent Number: 5,326,345
[45] Date of Patent: Jul. 5, 1994

[54] EYE FILTRATION PROSTHESES

[76] Inventor: Francis W. Price, Jr., 5511 Sunset La., Indianapolis, Ind. 46208

[21] Appl. No.: 971,072

[22] Filed: Nov. 3, 1992

Related U.S. Application Data

[63] Continuation-in-part of Ser. No. 744,875, Aug. 14, 1991, Pat. No. 5,171,213.

[51] Int. Cl.⁵ .................. A61F 2/14; A61M 5/00; A61M 35/00
[52] U.S. Cl. ........................... 623/4; 604/9; 604/294
[58] Field of Search .................. 604/8–10, 604/175, 264, 247, 250, 294; 623/4

[56] References Cited

U.S. PATENT DOCUMENTS 5,171,213 12/1992 Price, Jr. .................. 604/9

Primary Examiner—Randall L. Green
Assistant Examiner—Elizabeth M. Burke
Attorney, Agent, or Firm—Woodard, Emhardt, Naughton, Moriarty & McNett

[57] ABSTRACT

A technique and device for relieving intraocular pressure with a reduced risk of inflammation that may be caused by retrograde flow back into the eye. A unidirectional drainage device is implanted which allows fluid to flow away from the eye with a minimal pressure gradient (5 mm Hg. or less), and includes means to prevent retrograde flow. When implanted, the drainage passageway is initially restricted by a flow restrictor. After fibrosis has occurred to prevent excessive drainage that might cause hypotony, the flow restrictor is severed to allow the free flow of fluid away from the eye, with inflammatory debris being prevented from reentering the eye. In one embodiment, the flow restrictor includes barbs which hold it to the device after it has been severed, thereby preventing the flow restrictor from floating freely within the eye after it has been cut.

7 Claims, 12 Drawing Sheets

EYE FILTRATION PROSTHESES

REFERENCE TO RELATED APPLICATION

This application is a continuation-in-part of co-pending U.S. Pat. application, Ser. No. 07/744,875, filed on Aug. 14, 1991 and entitled A New Technique For Fistulization Of The Eye And An Eye Filtration Prosthesis Useful Therefor which application is now U.S. Pat. No. 5,171,213.

BACKGROUND OF THE INVENTION

1. Field of the Invention:

The field of this invention is eye surgery. More specifically, this invention relates to surgical techniques for fistulization of the eye and to devices useful in such procedures.

2. Description of the Prior Art:

It is well known in the field of Ophthalmology that chronic inflammation within eye can cause deterioration and gradual opacification of the cornea by slowly damaging the cells on the inside surface of the cornea. Chronic inflammation within the eye has also been shown to cause problems with the retina. It is particularly important to avoid chronic inflammation in connection with glaucoma surgery, which is performed when a patient develops difficulties from increased pressure within the eye. This increased pressure can cause damage to the optic nerve, which may be manifested by a loss of vision, or may cause changes in the visual field. Most cases of glaucoma are treatable by topical or oral medications, however in many cases the patient must undergo glaucoma surgery to relieve the pressure. A glaucoma surgical procedure typically utilizes some type of fistulization process to drain fluids out from within the eye. With some individuals, however, there is difficulty in maintaining adequate fistulization, in which case mechanical devices are often implanted in the eye to facilitate the outflow of fluid.

These mechanical devices fall into two categories: free flowing systems and pumps. Free flowing systems allow fluid to filter out of the eye, with the flow of fluid being restricted only by the size of the conduit and the development of scar tissue which forms around the filtering system. Pumping mechanisms operate to mechanically assist in the flow of fluid away from the eye.

When the eye is being drained of fluids, care must be taken to avoid hypotony, which is a condition where the internal pressure within the eye becomes lower than desired. A prolonged hypotony can lead to complications, such as shallowing or loss of the anterior chamber which can cause damage to the cornea. A hypotonic condition can also cause hemorrhaging in the posterior portion of the eye, which may result in a choroidal or retinal detachment, and also could possibly result in the loss of the eye itself. To prevent hypotony with a free flowing drainage system, sometimes sutures are placed around portions of the filtration tube to restrict the flow of fluid while scar tissue is developing. Once scarring has been formed around the filtering system, a sufficient natural restriction on drainage has been created to allow the suture to be removed and drainage to take place.

One significant disadvantage of the free flowing systems is that a large amount of inflammatory debris can sometimes pass in a retrograde fashion from the filtration system and filtering blebs back into the eye. While retrograde flow of inflammatory debris can occur at any time with such a system, this problem can be aggravated when the filtering tube is closed, as described above, to prevent hypotony. When ligatures are used to constrict the filtering tube, blood and debris fill the tube proximal to the ligature and, upon opening the filtration tube, a large amount of inflammatory debris is liberated within the eye despite the fact that initial fluid flow from the eye to the filtering system pushes the debris temporarily back up into the filtration system. This back flow of inflammatory debris into the eye is a potential cause of chronic inflammation of the eye, possibly resulting in the above described undersirable complications.

An example of a pump system for relieving intraocular pressure is shown in U.S. Pat. No. 4,554,918 to White. In order to avoid hypotony, an inherent pressure gradient is needed to be achieved across the White pump before fluid can flow through the pumping mechanism. It is suggested in U.S. Pat. No. 4,554,918 that this pressure gradient be in the range of 8-10 mm Hg. While this design characteristic of the White pump helps decrease the occurrence of hypotony immediately after implantation, sometimes the eye does not reach a sufficient pressure for fluid to exit, in which case this pump fails to function as a pressure relief mechanism. This pump also serves to restrict the retrograde flow of fluid, however debris has been found to clog the pumping mechanism, causing it to fail to function properly. U.S. Pat. No. 4,886,488 to White discloses a second pressure relief system which also operates upon the occurrence of a pressure gradient in the range of 8-10 mm Hg.

SUMMARY OF THE INVENTION

This invention relates to improvements for relieving intraocular pressure within the eye with a reduced risk of inflammation within the eye that may be caused by the retrograde flow of fluid and inflammatory debris back into the eye after a glaucoma surgical procedure has been performed. In the following description of the preferred embodiment, a technique is taught in which a unidirectional drainage device is implanted to drain fluids away from the eye. The device operates to allow fluid to flow away from the eye with a minimal pressure gradient (5 mm Hg. or less), and includes means to prevent retrograde flow. In one embodiment, at the time of implantation the drainage passageway is initially restricted or closed by a flow restrictor at a point downstream from the minimal pressure gradient unidirectional valve. Between the unidirectional valve and flow restrictor is a drainage trap in which debris is receivable without restricting the operativeness of the unidirectional valve. After sufficient scarring and fibrosis has occurred to prevent excessive drainage that might cause hypotony, the flow restrictor is removed to allow the free flow of fluid away from the eye, with inflammatory debris being prevented from reentering the eye by being either drained away or by being maintained within the drainage trap.

In a second described embodiment, the flow restrictor is located at the distal end of the receptor tube of the device within the eye, and acts to prevent the influx of fluids into the device from the eye during the initial period after implantation. Upon removal of the flow restrictor, the free flow of fluids away from the eye is allowed while retrograde flow back into the eye is prevented by the action of a unidirectional valve which is designed to permit the forward flow of fluid there through under low pressure gradient conditions.

In a third embodiment, the unidirectional valve is located within the device where the fluids from the connector tube enter into the drainage plate of the device. This third embodiment also incorporates a flow restrictor which includes barbs that hold the flow restrictor to the connector tube when the flow restrictor is severed to allow the free flow of fluid within the receptor tube. In this way, the flow restrictor is held to the device and not allowed to float freely within the eye after it has been cut.

It is an object of the present invention to provide an improved technique for relieving intraocular pressure which also reduces the risk of inflammation within the eye after glaucoma surgery by either preventing or minimizing the flow of fluid and inflammatory debris back into the eye.

It is a further object of the present invention to provide a new device which is useful for relieving intraocular pressure while also serving to reduce the risk of inflammation within the eye after glaucoma surgery has been performed.

These and other objects and advantages will be apparent from a reading of the following specification.

BRIEF DESCRIPTION OF THE DRAWINGS

In FIG. 1a, drainage is restricted by flow restrictor 53.

In FIG. 2a, flow restrictor 53 has been removed to allow the free flow of fluids away from the eye.

In FIG. 3a, prosthesis 50 is closed by flow restrictor 53 to restrict the flow of fluid away from the eye while scar tissue is in the process of forming around the implanted device. In FIG. 3b, prosthesis 50 has been opened by removing flow restrictor 53 to allow the unrestricted flow of fluid away from the eye after scar tissue has been adequately formed to prevent excessive drainage that might cause hypotony.

In FIG. 4a, drainage is restricted by flow restrictor 53' which is located at the distal end of a receptor tube 51' within the eye. FIG. 4b shows a side elevational view of the implanted prosthesis of FIG. 4a in relation to the eye on which it has been implanted, with a portion of eye 10 cut away to expose the location of flow restrictor 53' at the distal end of a receptor tube 51' within the eye.

In FIG. 5a, valve 56' is closed, preventing the backflow of fluid into the eye under negative pressure gradient conditions. In FIG. 5b, a positive pressure gradient has opened valve 56' thereby allowing the unrestricted flow of fluid away from the eye.

FIG. 6a shows unidirectional valve 156 of filtration prosthesis 150 to be located where the fluids from connector tube 152 enter into drainage plate 154. FIG. 6b shows a side elevational view of the implanted prosthesis of FIG. 6a in relation to the eye on which it has been implanted, with a portion of eye 10 cut away to expose the location of flow restrictor 153 at the distal end of a receptor tube 151 within the eye. FIG. 6b also shows the location of unidirectional valve 156 within drainage plate 154 in dashed lines.

FIG. 7a is a partial fragmentary view of prosthesis 150, cross-sectioned along lines A—A in FIG. 6a to show valve 156 within drainage plate 154 at the entry point of connector tube 152 into drainage plate 154. FIG. 7b is a partial fragmentary view of prosthesis 150, cross-sectioned along lines B—B in FIG. 6a, showing valve 156 within drainage plate 154 in a closed position. FIG. 7c shows the view of FIG. 7b with valve 156 in an open position.

FIG. 8a is a partial side elevational view of receptor tube 151 with flow restrictor 153 attached thereabout. Also shown in FIG. 8a are barbs 153a of flow restrictor 153 which are embedded into receptor tube 151 at the point of restriction. FIGS. 8b and 8c are cross-sectioned views of receptor tube 151 along lines C—C of FIG. 8a with flow restrictor 153 positioned thereon. FIG. 8b shows flow restrictor 151 restricting the flow of fluid through receptor tube 151, with barbs 153a of flow restrictor 153 embedded into receptor tube 151. FIG. 8c shows flow restrictor 153 remaining attached to receptor tube 151 by barbs 153a, after flow restrictor 153 has been severed to allow the free flow of fluids through receptor tube 151. In FIGS. 8a-c, the interior structure of receptor tube 151 is shown in dashed lines.

DESCRITPION OF THE PREFERRED EMBODIMENT

Figure 1A:
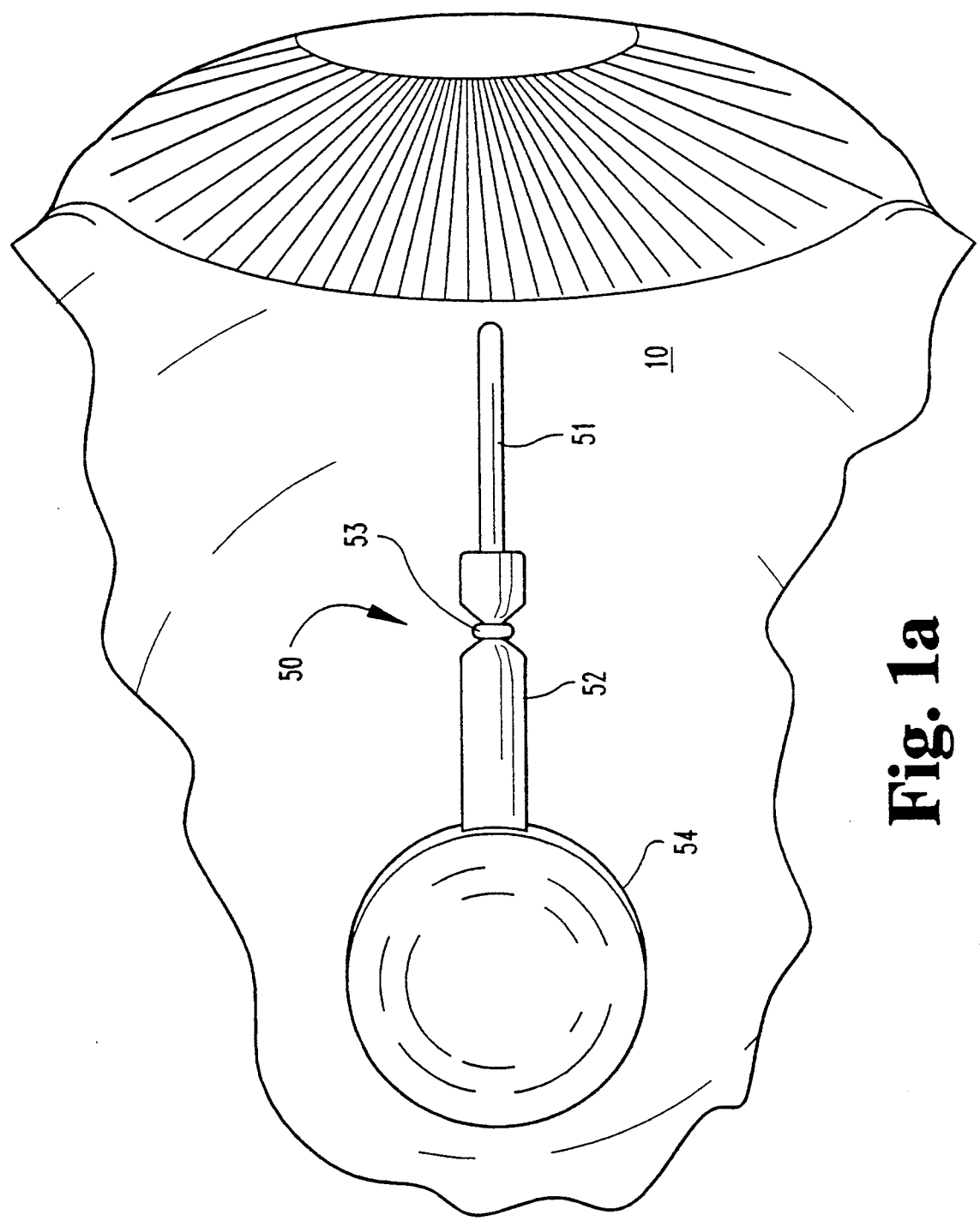
FIG. 1a shows an eye filtration prosthesis 50 implanted on an eye in position to relieve excessive intraocular pressure by draining fluid away from the eye.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1B:
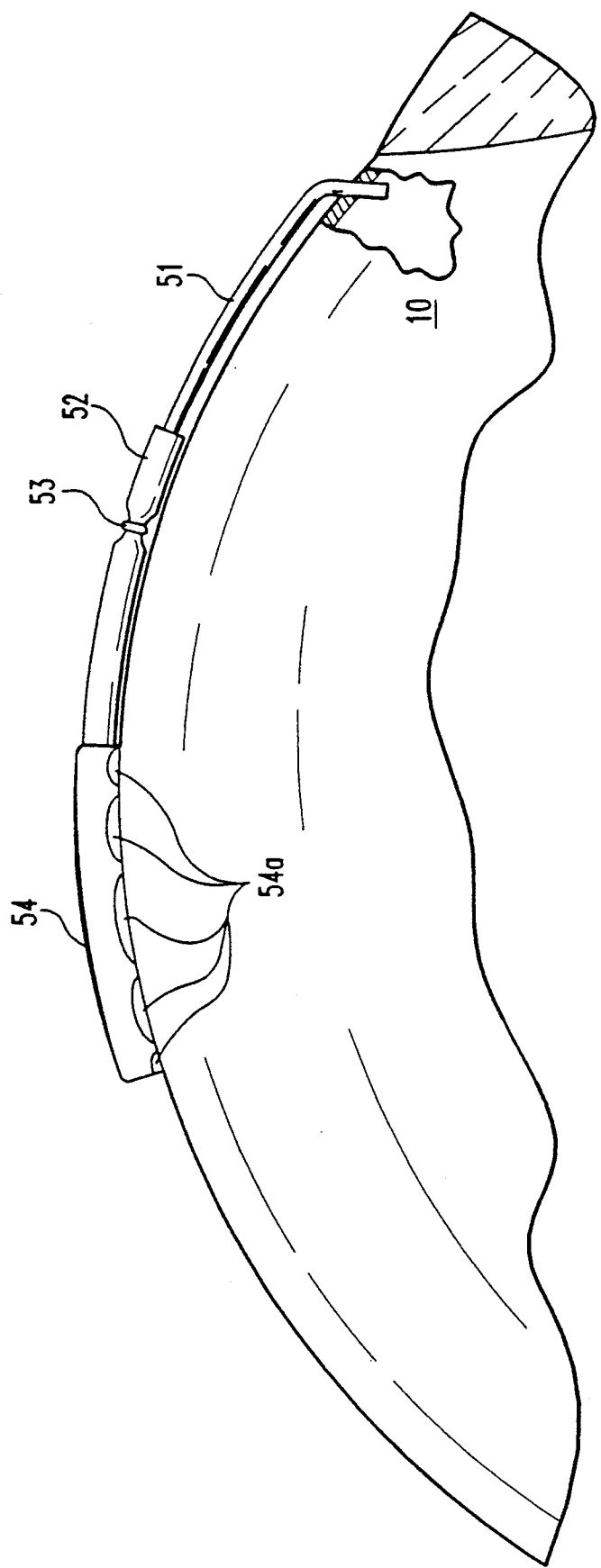
FIG. 1b shows a side elevational view of the implanted prosthesis of FIG. 1a in relation to the eye on which it has been implanted, with a portion of the eye being shown in cut away fashion to show the portion of prosthesis 50 extending within the eye.

Referring now to the drawings, FIG. 1a shows an eye filtration prosthesis 50 implanted on an eye in position to relieve excessive intraocular pressure by draining fluid away from eye 10. In FIG. 1a, prosthesis 50 is seen to include receptor tube 51, connector tube 52, flow restrictor 53, and drainage plate 54. FIG. 1b shows a side elevational view of implanted prosthesis 50 in relation to eye 10 on which it has been implanted. In FIG. 1b, the end portion of receptor tube 51 is seen to extend into the anterior chamber of eye 10, where fluids are to be received into prosthesis 50 to relieve intraocular pressure within eye 10. Receptor tube 51 may also be positioned within the posterior chamber of the eye in conjunction with a pars plana vitrectomy. Also shown in FIG. 1b are drainage ports 54a, located about the circumference of drainage plate 54, at which location drained fluids are to exit prosthesis 50.

In FIGS. 1a and 1b, drainage away from eye 10 is restricted by flow restrictor 53, which restricts or totally closes connector tube 52 to prevent the free flow of fluid. Prosthesis 50 is initially left in this flow restricted condition at the time of implantation to prevent hypotony while scar tissue is formed around prosthesis 50. As mentioned, flow restrictor 53 may serve to either restrict, or totally close off, the flow of fluid through prosthesis 50 during this time. If formed to restrict, but not totally close off the flow of fluid, then restrictor 53 may operate to allow a minimal flow under high pressure gradient conditions (20 mm Hg or more). This restricted interim flow over a high pressure gradient does not create a risk of hypotony during the initial period after implantation, and advantageously provides for the partial alleviation of excessive pressure during the formation of fibrosis. Alternatively, restrictor 53 may be placed to fully close off the flow of fluid within prosthesis 50, in which case no drainage occurs through prosthesis 50 until the required scarring is formed, and restrictor 53 is subsequently removed.

Figure 2A:
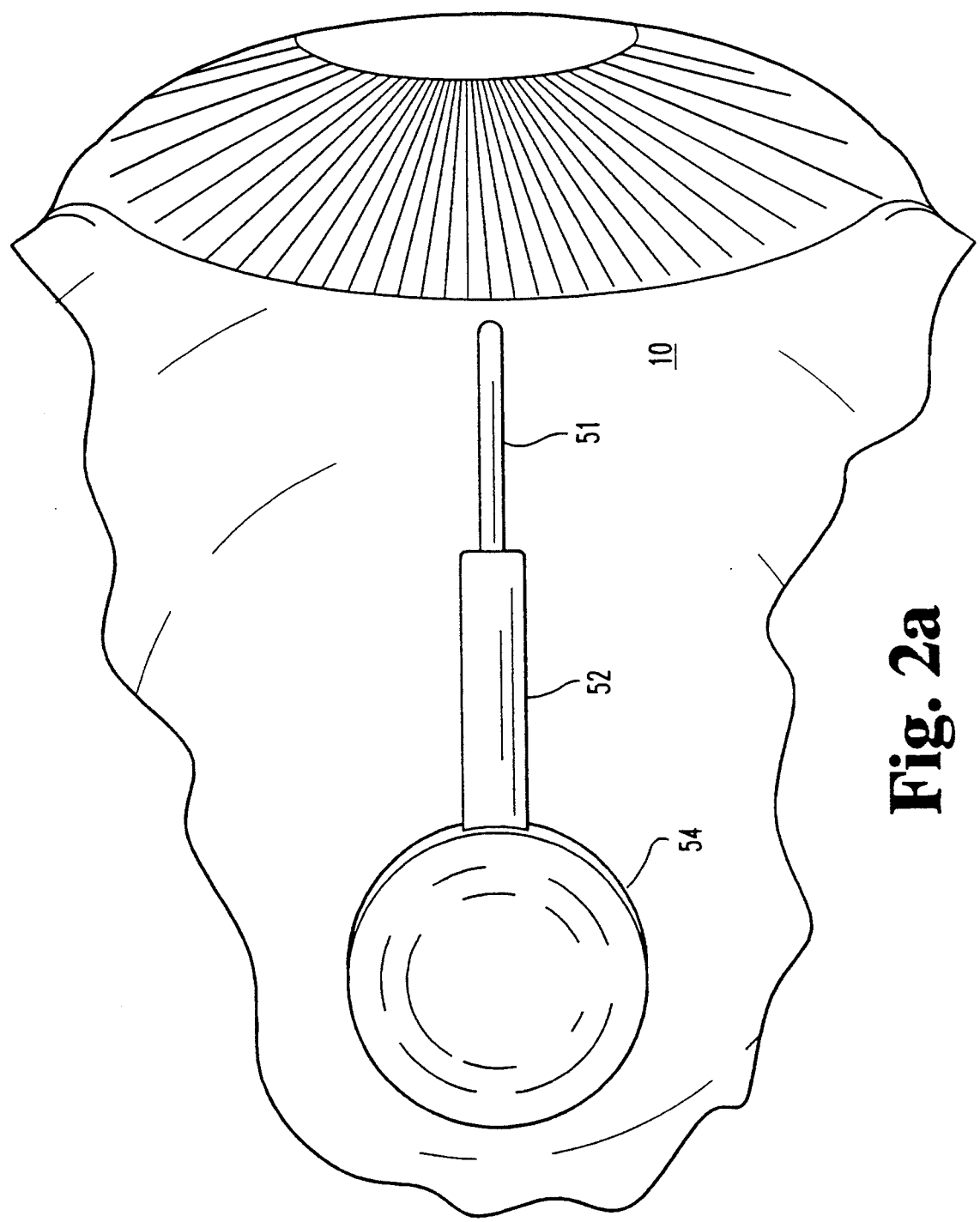
FIG. 2a shows the implanted eye filtration prosthesis 50 of FIG. 1a after scarring has developed around drainage plate 55.
Figure 2B:
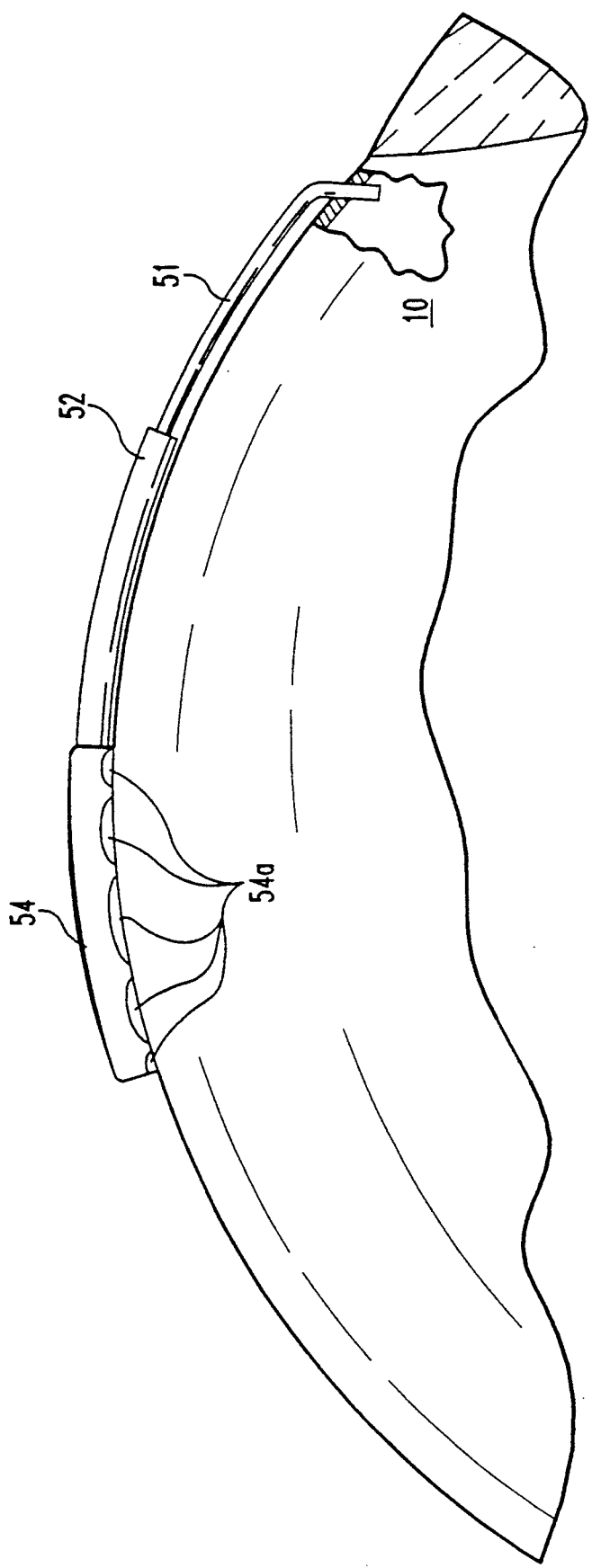
FIG. 2b is a side elevational view of the prosthesis shown in FIG. 2a, with a portion of the eye being shown in cut away fashion to show the portion of prosthesis 50 extending within the eye.

FIG. 2a shows the implanted eye filtration prosthesis 50 of FIG. 1a after scarring has developed around drainage plate 54. After sufficient scarring and fibrosis has occurred to prevent excessive drainage that might cause hypotony, flow restrictor 53 is removed to allow the free flow of fluid away from eye 10. In FIG. 2a, flow restrictor 53 has been removed to allow the free flow of fluids away from eye 10. FIG. 2b is a side elevational view of prosthesis 50 shown in FIG. 2a, with flow restrictor 53 having been removed to allow for drainage to occur.

Implanted and utilized as described above, prosthesis 50 is useful for relieving intraocular pressure within the eye while avoiding the possibility of creating hypotony within the eye that could potentially cause severe damage to the eye. Furthermore, prosthesis 50 is operable to assist in partially relieving intraocular pressure over high pressure gradients (20 mm Hg or more) immediately after implantation, and relieves intraocular pressure at low pressure gradients (less than 5 mm Hg) after fibrosis has been formed and flow restrictor 53 has been removed. This is accomplished by means of a low pressure gradient unidirectional valve 56 described below in relation to FIGS. 3a and 3b. Prosthesis 50 also serves to reduce the risk of inflammation within the eye after glaucoma surgery has been performed by preventing the back flow of fluids into the eye which might cause such inflammation to develop.

Figure 3A:
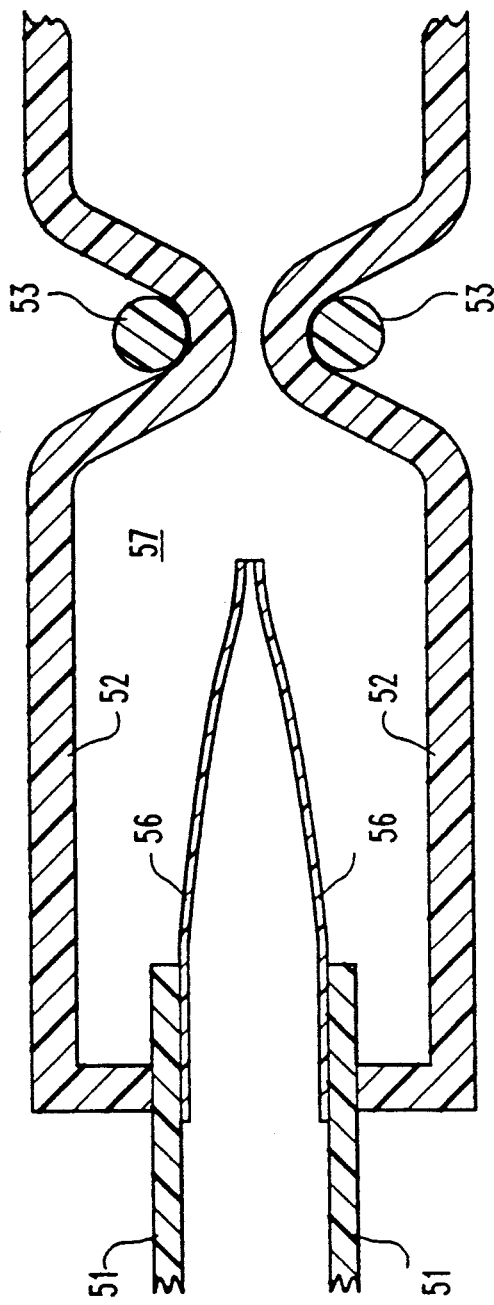
FIGS. 3a and 3b are fragmentary cross-sectional views of a portion of prosthesis 50 which includes unidirectional valve 56, trap 57, and flow restrictor 53, and illustrate the operation of unidirectional flow away from the eye.
Figure 3B:
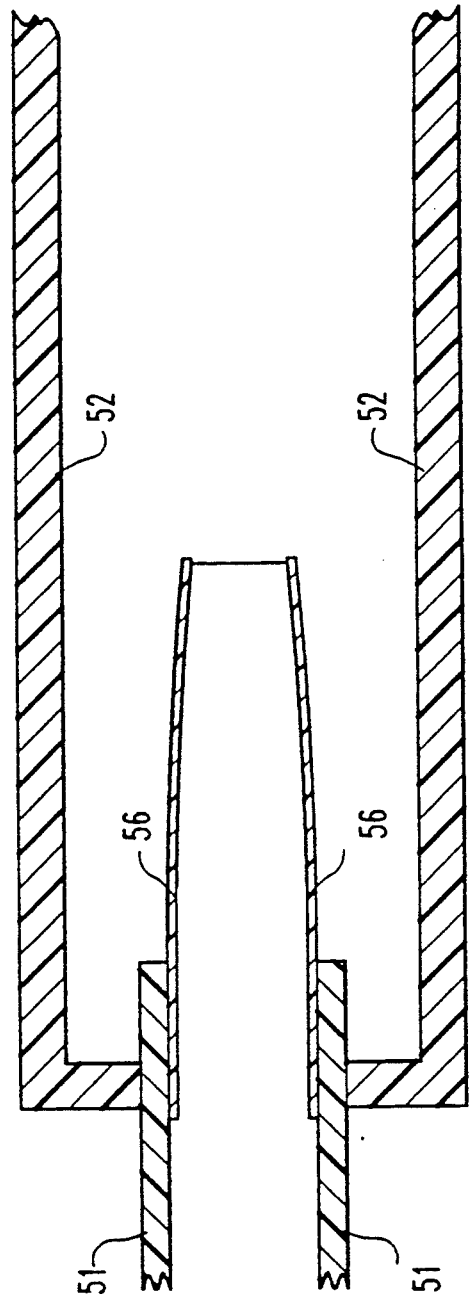

The operation of prosthesis 50 to provide for relief of intraocular pressure under low pressure gradient conditions and the prevention of retrograde flow into the eye will now be discussed in relation to FIGS. 3a and 3b. FIGS. 3a and 3b are fragmentary cross-sectional views of the portion of prosthesis 50 which includes unidirectional valve 56, trap 57, and flow restrictor 53. Unidirectional valve 56, trap 57, and flow restrictor 53 operate, in conjunction, to permit unidirectional flow away from the eye and prevent the retrograde flow of fluids and debris back into the eye which could cause the development of inflammation in the eye to occur.

In FIG. 3a, prosthesis 50 is closed by flow restrictor 53 to restrict the flow of fluid away from the eye while scar tissue is in the process of forming around the implanted device. As discussed above, flow restrictor 53 may be configured to allow for the minimal flow of fluid under high pressure gradient conditions, or alternatively, to totally close off the flow of fluid through prosthesis 50. When prosthesis 50 is in this flow restricting condition, inflammatory debris is allowed to pass through unidirectional valve 56 and flow restrictor 53 should be sized to adequately accommodate collected debris during the period of closure without unduly restricting the operation of valve 56.

Unidirectional valve 56 is designed to allow the free flow of fluid away from the eye under low pressure gradient conditions. Ideally, unidirectional valve 56 would operate in a near zero pressure gradient environment, although, in reality, it is believed that unidirectional valve 56 should open with the development of a positive pressure gradient of 5 mm Hg or less. Valve 56 is formed in a "wet straw" configuration where a generally circular cross-section is drawn to a flatten end. With this configuration, a positive pressure gradient serves to open the "wet straw" to allow fluid to flow, whereas a negative pressure gradient will cause valve 56 to collapse on itself to prevent retrograde flow. Because of its pliability and its low frictional properties, Teflon is a suitable material for the construction of valve 56, although other materials may be found to function satisfactorily. Also, it is to be noted that other specific valve configurations which provide for unidirectional flow under low pressure gradient conditions may be suitably incorporated into the present invention, as contemplated by the inventor.

In FIG. 3b, prosthesis 50 has been opened by the removal of flow restrictor 53 to allow the unrestricted flow of fluid away from eye 10 after scar tissue has been adequately formed to prevent excessive drainage that might cause hypotony. Flow restrictor 53 is formed as a ring or loop type closure about the circumference of connector tube 52, which is suitably made of silicon material. Flow restrictor 53 may be made of any appropriate plastic or suture material that would serve to cause a restriction in connector tube 52. Flow restrictor 53 can be removed by simply cutting it away to allow tube 52 to return to its original configuration, as shown in FIG. 3b. In FIG. 3b, it is seen that the positive pressure gradient causes valve 56 to open to a generally circular configuration to allow fluids to drain away from eye 10. Inflammatory debris which has collected in trap 57 is flushed away, or may remain within connector tube 52, however, such debris is prevented from reentering eye 10 owing to the unidirectional action of valve 56.

Figure 4A:
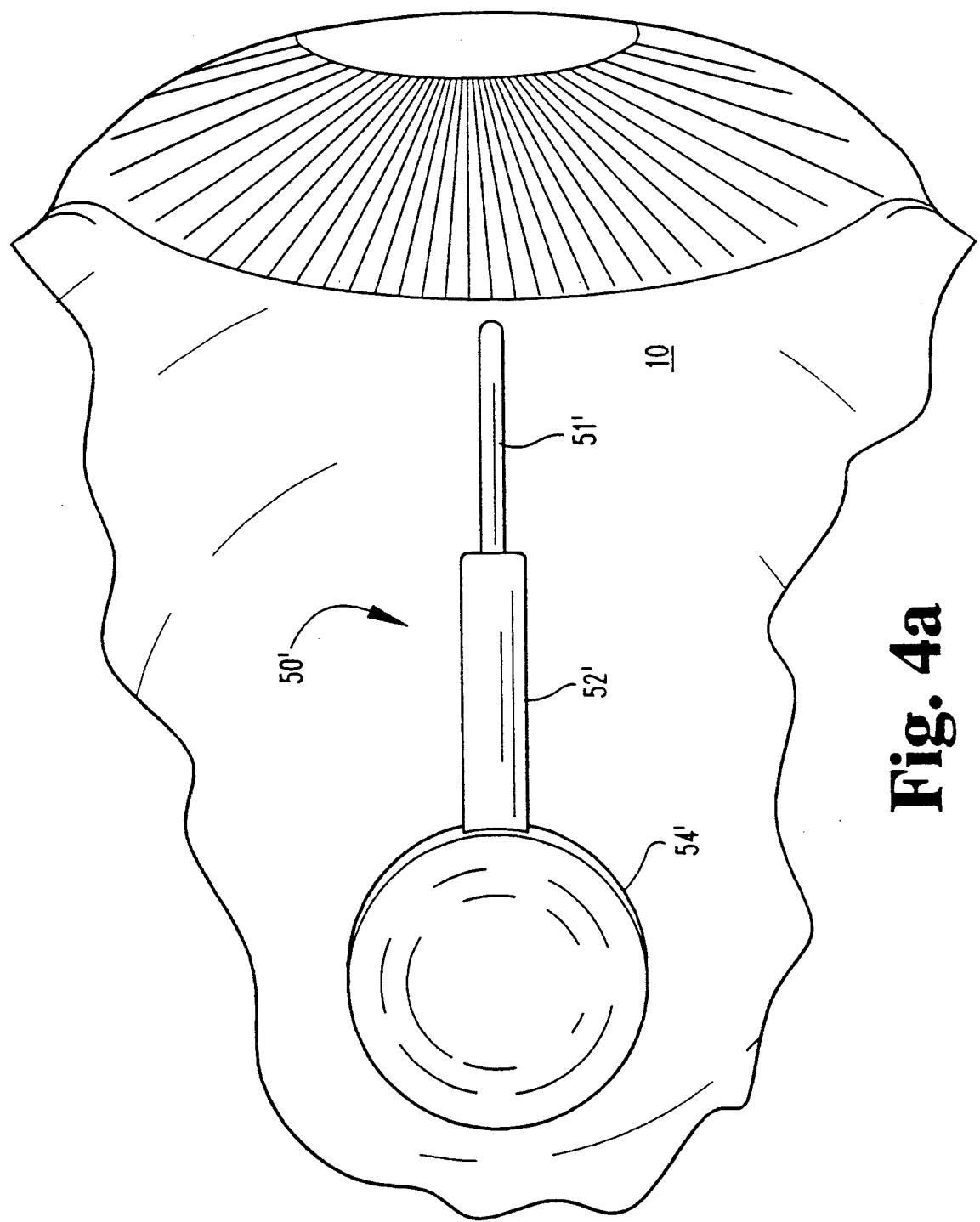
FIGS. 4a and 4b show a second eye filtration prosthesis 50' implanted on an eye in position to relieve excessive intraocular pressure by draining fluid away from the eye.
Figure 4B:
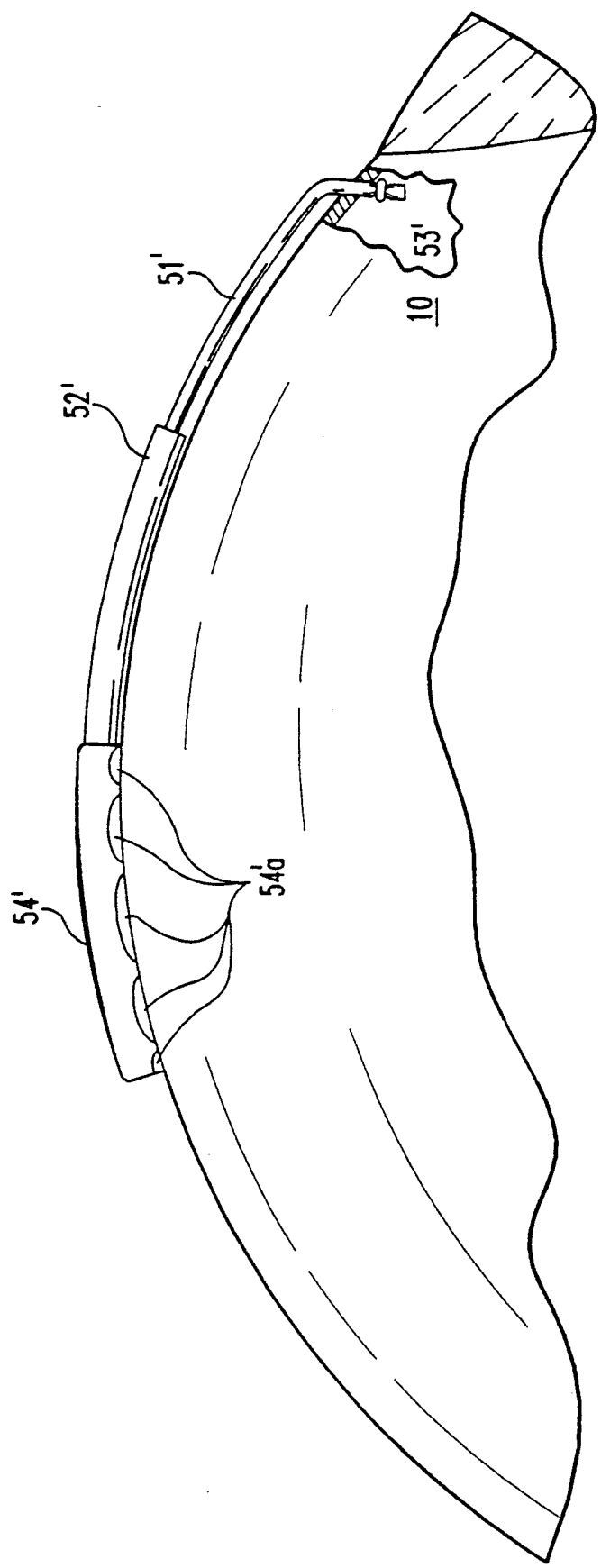

FIGS. 4a and 4b show a second eye filtration prosthesis 50' implanted on an eye in position to relieve excessive intraocular pressure by draining fluid away from the eye. Except as specifically described, the structure and operation of prosthesis 50' is the same as prosthesis 50, with primed numbered elements corresponding to same relative unprimed numbered elements of prosthesis 50. In FIG. 4a, drainage is restricted by flow restrictor 53' which is located at the distal end of a receptor tube 51' within the eye. FIG. 4b shows a side elevational view of the implanted prosthesis of FIG. 4a in relation to the eye on which it has been implanted, with a portion of eye 10 cut away to expose the location of flow restrictor 53' at the distal end of a receptor tube 51' within the eye 10. Flow restrictor 53', by being located at the distal end of the receptor tube of the device within the eye, acts to prevent the influx of fluids into the device from the eye during the initial period after implantation. Flow restrictor 53' may be removed from its restricting position on receptor tube 51 within eye 10 by the application of a laser beam of short duration on flow restrictor 53'. Upon removal of flow restrictor 53', the free flow of fluids away from the eye is allowed while retrograde flow back into the eye is prevented in the same manner as described in relation to prosthesis 50.

Figure 5A:
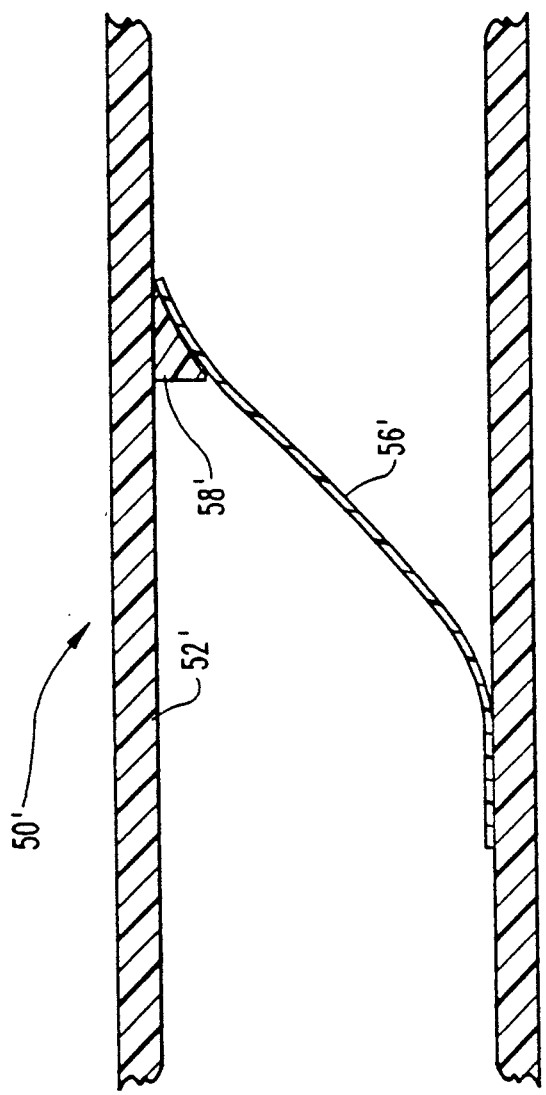
FIGS. 5a and 5b show an alternative valve configuration for inclusion with prosthesis 50'.
Figure 5B:
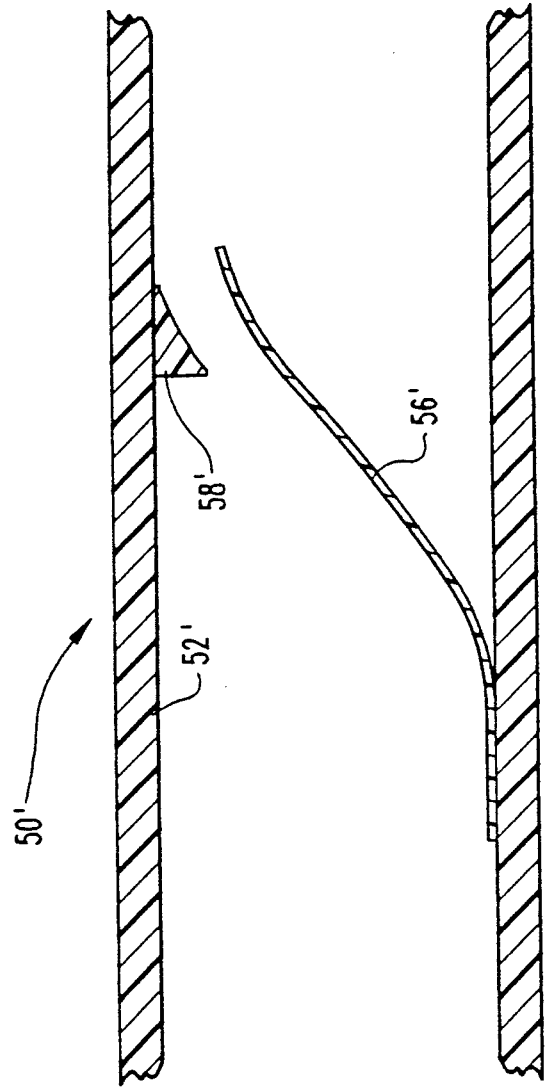

FIGS. 5a and 5b show an alternative valve configuration for inclusion with prosthesis 50'. In FIG. 5a, valve 56' is formed as a flap and is shown in a closed position preventing the backflow of fluid into the eye under negative pressure gradient conditions. Wedge 58' provides reinforcement to flap valve 56' to aid in preventing a negative pressure gradient from pushing valve 56' open backwardly. In FIG. 5b, a positive pressure gradient is shown to have opened valve 56' to allow the unrestricted flow of fluid away from the eye.

Figure 6A:
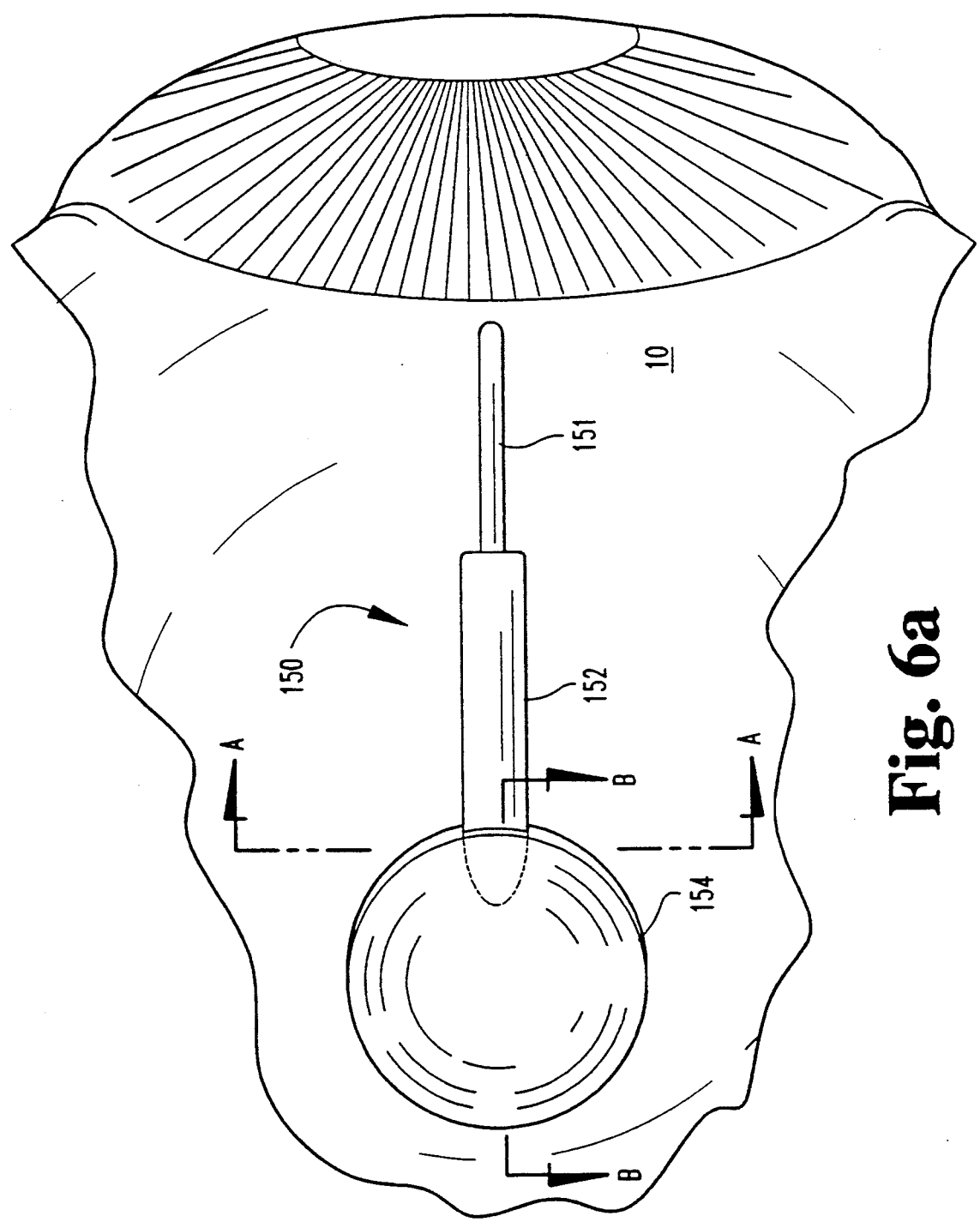
FIGS. 6a and 6b show a third eye filtration prosthesis 150 implanted on an eye. In dashed outline form.
Figure 6B:
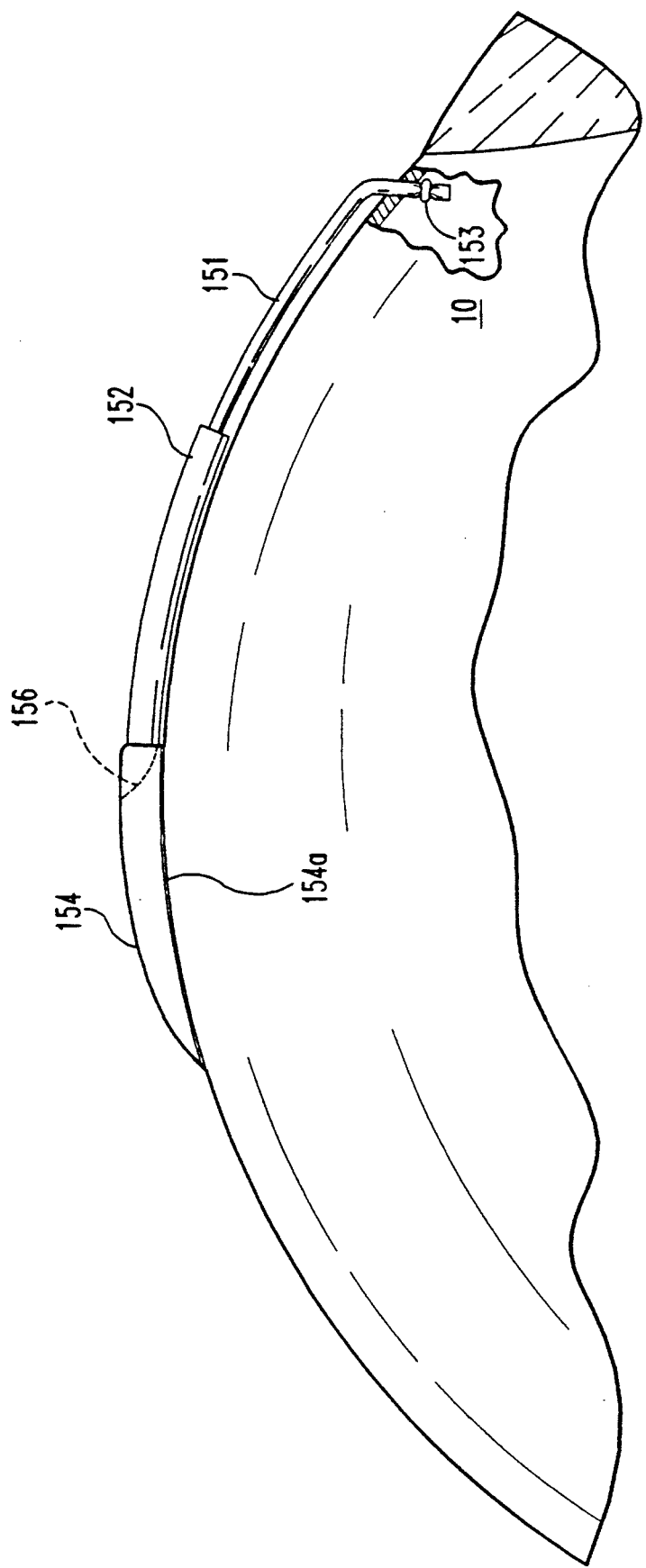

FIGS. 6a and 6b show a third eye filtration prosthesis 150 implanted on eye 10. As shown in these figures, unidirectional valve 156 is located within drainage plate 154 where fluids from connector tube 152 enter into drainage plate 154. After entering drainage plate 154, fluids then exit prosthesis 150 about the periphery 154a of drainage plate 154, whereby the conducting of fluids away from the eye is completed.

Figure 7A:
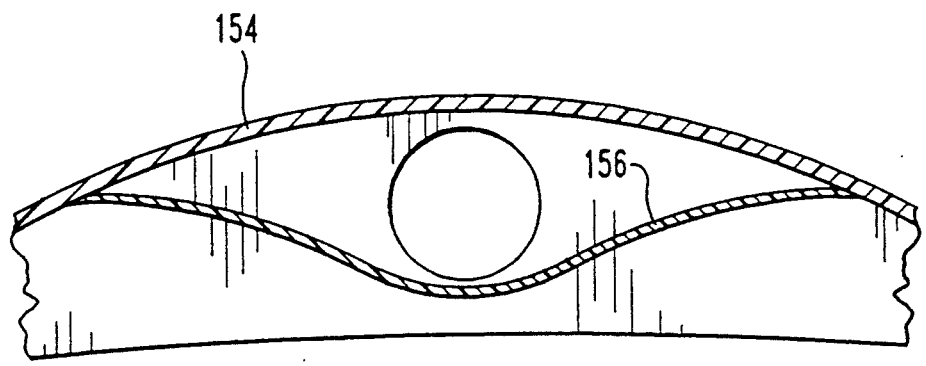
FIGS. 7a, 7b, and 7c show, in detail, the structure of unidirectional valve 156 within drainage plate 154.
Figure 7B:
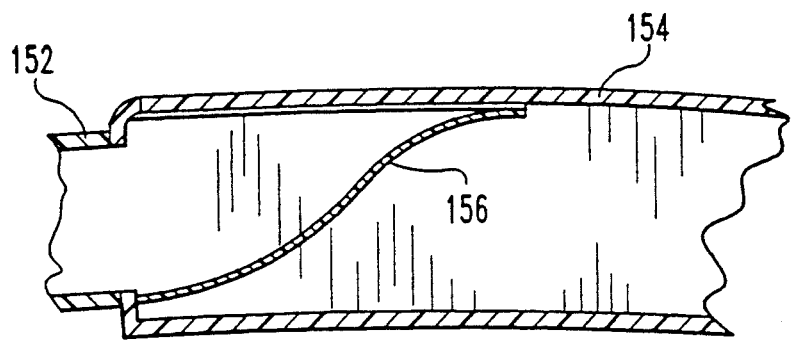
Figure 7C:
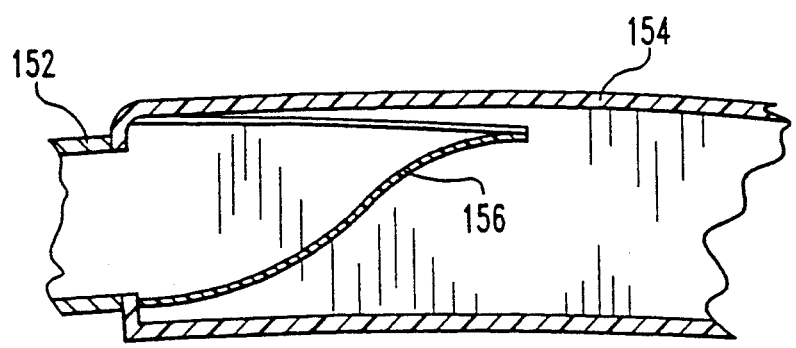

FIGS. 7a, 7b, and 7c show, in further detail, the structure of unidirectional valve 156 within drainage plate 154, and serve to demonstrate the operation of valve 156 within drainage plate 154. As seen in FIG. 7b, valve 156 has a flap configuration which lies against plate 154 when closed by negative pressure to prevent the reflux of fluid back into the eye. As is shown in FIG. 7c, the occurrence of a positive pressure gradient causes valve 156 to be pushed away from drainage plate 154 to thereby allow fluid to freely flow away from the eye.

Figure 8A:
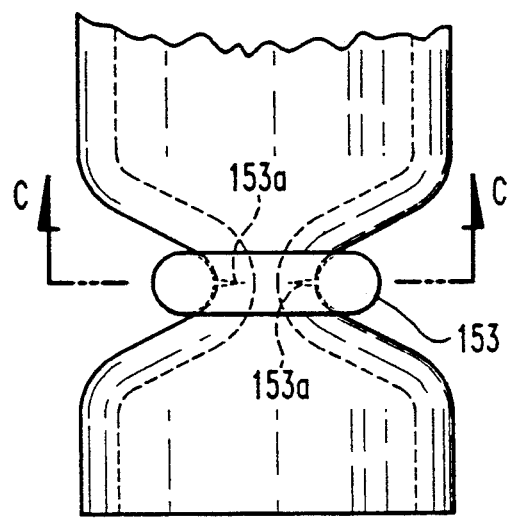
FIGS. 8a, 8b, and 8c illustrate the manner of attachment of flow restrictor 153 to receptor tube 151.
Figure 8B:
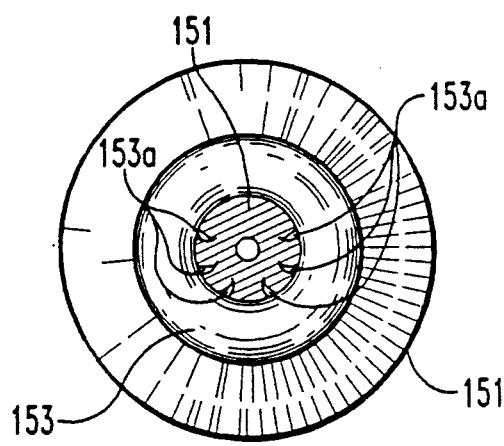
Figure 8C:
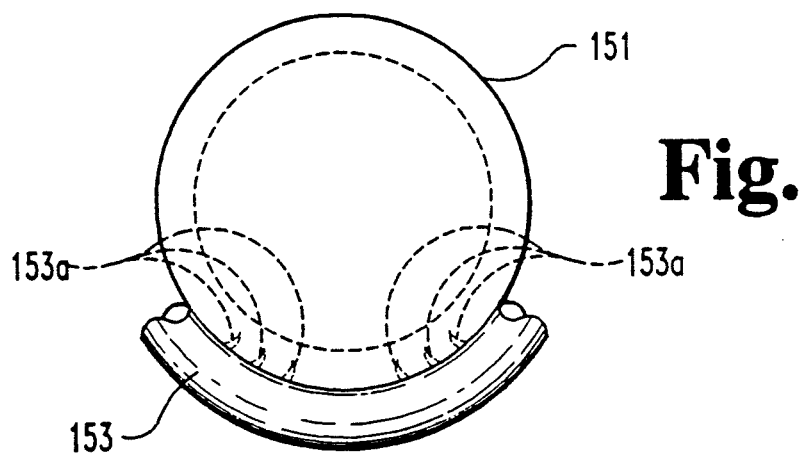

FIGS. 8a, 8b, and 8c illustrate the manner of attachment of flow restrictor 153 to receptor tube 151 such that restrictor 153 maintains its attachment to receptor tube 151 after it has been released from restricting the flow of fluid through receptor tube 151. As shown in these figures, barbs 153a of flow restrictor 153 are embedded into receptor tube 151 at the point of restriction on receptor tube 151. As is further shown in FIG. 8c, flow restrictor 153 maintains its attachment to receptor tube 151 by barbs 153a even after flow restrictor 153 has been severed to allow the free flow of fluids through receptor tube 151. In this way, barbs 153a serve the purpose of holding flow restrictor 153 to receptor tube 151 after flow restrictor 153 has been severed to prevent flow restrictor 153 from being allowed to float freely within the eye after it has been cut. When prosthesis 150 is later removed, flow restrictor 153 is thus also removed from within the eye along with receptor tube 151.

Barbs 153a should be constructed of sufficiently rigid material so that they are able to pierce and be retained within receptor tube 151. One suitable material for this purpose is believed to be fiberglass. Barbs 153a may also be configured for various angles of entry into receptor tube 151 and at various locations about the circumference thereof to maintain stable attachment thereto. Alternative structures for maintaining attachment are contemplated as well. For instance, barbs may be mounted into the receptor tube element of the device rather than into the flow restricting element, and designed to pierce and retain the flow restricting element. Also, the flow restricting element may be satisfactorily attached by the use of other manners of attachment, such as with loops, ties, or clips.

In the figures, flow restrictors 53, 53', and 153 are shown as rings. It is also to be mentioned that alternative configurations for this flow restricting element are contemplated as well. For instance, this flow restricting element may be formed as an interlocking loop, or other type of clip configuration which generally serves the purpose of constricting receptor tube 151 to restrict the flow of fluid therethrough. Accordingly, while the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An eye filtration prosthesis for relieving intraocular pressure from within an eye, the eye having an interior portion and a periphery thereabout, said device comprising:

conduit means for receiving fluid from within the interior portion of the eye and draining fluid away from the eye; said conduit means including a drainage tube and a drainage plate attached thereto;

drainage port means for draining fluid received by said conduit means out of said prosthesis at a location exterior of the eye; said drainage port means being located about the periphery of said drainage plate;

a low pressure gradient unidirectional valve within said conduit means, said valve including means for allowing fluid to pass away from the eye under low pressure gradient conditions and preventing retrograde flow back into the eye; and flow restrictor means for restricting fluid from flowing within said conduit means away from the eye; and wherein said prosthesis, when implanted, is operable in a flow restricted state in which said flow restrictor means restricts fluid from flowing within said conduit means away from the eye and out of said prosthesis; and a free flow state in which said flow restrictor means has been deactivated to allow fluid to freely flow there past, with said valve allowing fluid to flow though said conduit means under low pressure gradient conditions while preventing retrograde flow back into the eye.

2. The eye filtration prosthesis of claim 1 wherein said unidirectional valve is located within said drainage plate.

3. The eye filtration prosthesis of claim 1 wherein said flow restrictor means is attached about said conduit means within the eye, and wherein said flow restrictor means includes attachment means for maintaining attachment to said conduit means after said flow restrictor means has been released to allow fluids to flow freely through said conduit means, whereby said flow restrictor means is prevented from floating freely within the eye.

4. The eye filtration prosthesis of claim 3 wherein said attachment means includes at least one barb projecting into said conduit means to maintain attachment thereto after said flow restrictor means has been released to allow fluids to flow freely through said conduit means.

5. The eye filtration prosthesis of claim 4 wherein said barb is made of fiberglass material.

6. The eye filtration prosthesis of claim 1 in which said low pressure gradient unidirectional valve allows fluid to flow there through at a pressure gradient of less than about 5 mm Hg. across said valve.

7. The eye filtration prosthesis of claim 2 in which said valve is formed in a flap configuration within said drainage plate, and wherein said valve lies against said plate when closed by negative pressure to prevent fluid from refluxing back into the eye, and wherein a positive pressure gradient is created to cause said valve to be pushed away from said drainage plate to thereby allow fluid to freely flow away from the eye.

* * * * *